(12) United States Patent
Kitani et al.

(10) Patent No.: US 7,824,364 B2
(45) Date of Patent: Nov. 2, 2010

(54) LIQUID-MIXING INFUSOR

(75) Inventors: Ichiro Kitani, Shizuoka-ken (JP); Shigeaki Funamura, Shizuoka-ken (JP)

(73) Assignee: Tyco Healthcare Group LP, Mansfield, MA (US)

( * ) Notice: Subject to any disclaimer, the term of this patent is extended or adjusted under 35 U.S.C. 154(b) by 472 days.

(21) Appl. No.: 11/796,414

(22) Filed: Apr. 27, 2007

(65) Prior Publication Data
US 2007/0255202 A1    Nov. 1, 2007

(51) Int. Cl.
*A61M 37/00* (2006.01)
(52) U.S. Cl. ....................................... 604/82
(58) Field of Classification Search ............ 604/19
See application file for complete search history.

(56) References Cited

U.S. PATENT DOCUMENTS

| 5,474,526 A | 12/1995 | Danielson et al. |
| 2006/0089603 A1 | 4/2006 | Truitt et al. |
| 2007/0175485 A1 | 8/2007 | Funamura et al. |

FOREIGN PATENT DOCUMENTS

| DE | 196 50 664 C1 | 2/1998 |
| EP | 0 193 266 | 9/1986 |
| EP | 1 234 596 A1 | 8/2002 |
| EP | 1234596 A1 * | 8/2002 |
| EP | 1 627 658 A1 | 2/2006 |
| EP | 1 790 377 A1 | 5/2007 |
| EP | 1 790 378 A1 | 5/2007 |
| GB | 1 482 052 A | 8/1977 |
| JP | 01025844 A | 1/1989 |
| WO | WO 2004/039446 A1 | 5/2004 |

OTHER PUBLICATIONS

European Search Report from Application No. 07002924.4-1526 mailed Aug. 8, 2007.

* cited by examiner

*Primary Examiner*—Nicholas D Lucchesi
*Assistant Examiner*—Jason Flick

(57) ABSTRACT

A liquid mixing infusor includes a main body defining an internal chamber and has an upstream port, a downstream port and a confluent port. Each port is fluidly couplable with the internal chamber. A valve may be mounted within the internal chamber of the main body and is adapted for rotational movement between a blocking position interrupting fluid flow between the confluent port and one of the upstream port and the downstream port and between the upstream port and the downstream port, and a flow position permitting fluid flow between the upstream port and the downstream port. A manually manipulative member is mounted relative to the main body and operatively connected to the valve. The manipulative member is movable to cause corresponding movement of the valve between the blocking position and the flow position.

17 Claims, 18 Drawing Sheets

LIQUID-MIXING INFUSOR

BACKGROUND

1. Technical Field

This disclosure pertains to a liquid-mixing infusor used in the medical field, connected to a plurality of infusion tubes, and equipped with a plurality of branch tubes and capable of switching the connection or blocking section of respective branch tubes.

2. Description of Art

The provision of normal saline solution, drug solution, into the body of a patient has been carried out previously by using infusion tubes. To prevent air from being mixed inside such infusion tubes and entering the body together with normal saline solution or drug solution, an air trap is installed in an infusion tube, and any air is trapped in this air trap, shown for example in Japanese Kokai Utility Model Application No. Sho 48[1973]-68994 (JP 48068994U).

In the case of this air trap, a portion of the horizontal area of a flow path extending in the horizontal direction is interrupted, a trap space is installed above this interruption, one end of the flow path from one direction is bent upwards and connected to one end of the trap space. One end of the flow path extending in the other direction is bent upwards and connected to the other end of the trap space. Namely, it is configured to have an inverted U-shaped portion equipped with a trap space formed in the flow path, to allow any air to be trapped in the trap space and prevent any air from entering the body.

SUMMARY

The air trap described above is used for an infusion tube for administering one kind of normal saline solution or drug solution, and no administration of multiple normal saline, drug solutions, is possible. Therefore, a liquid-mixing infusor to administer a plurality of normal saline or drug solutions by connecting or blocking a plurality of infusion tubes, but, in such a liquid-mixing infusor, it is difficult to prepare a structure preventing air from entering the body.

This disclosure has been created for circumstances as described above to provide a liquid-mixing infusor making it possible to remove any air in liquids and to connect or block any optional branch tubes among a plurality of branch tubes.

To accomplish the above objective, the liquid-mixing infusor of this disclosure is characterized with respect to the configuration by being equipped with a liquid mixing infusor main body including a chamber, the central portion of which is formed in a cylindrical shape with its axial direction set vertically, a branching portion formed above the chamber and equipped with a connectable or interruptible flow path to the inside of the chamber, and pair of branch tubes extending outwards from both sides of the peripheral surface of the center portion of the chamber and respectively having flow paths connected to the inside of the chamber; a valve installed inside the chamber in a rotatable state in the periaxial direction of the chamber and blocking between the pair of branch tubes and the chamber or connecting at least one of the pair of branch tubes and inside of the chamber through the branching portion; and a rotary portion extending outside of the chamber from the valve and having an operation portion rotatable in the periaxial direction of the chamber on the outside of the chamber.

The liquid-mixing infusor of this disclosure configured as described above has a rotation portion including a valve rotatable in the periaxial direction of the chamber and an operation portion extending out of the chamber from the valve and rotatable on the outer side of the chamber. Moreover, it is configured so that the valve can connect or block between the pair of branch tubes and the inside of the chamber by rotating the operation portion. Namely, this valve allows blocking between the pair of branch tubes and chamber or connection of tubes and chamber, and moreover, it allows one of the pair of branch tubes and the inside of the chamber to be connected.

Furthermore, by connecting the flow path of the branching portion to the chamber, it is possible to connect the flow path of the branching portion to one or both of the pair of branch tubes. As a result, it is possible to supply one or two kinds of drug solutions to the patient's body. In addition, if a drug solution is allowed to flow in a flow path formed by connecting between the pair of branch tubes and inside the chamber, the drug solution passes the branching portion formed above the chamber.

Specifically, the branching portion has a space formed above the flow path connecting one branch tube to the other branch tube through the chamber. As a result, if a drug solution is allowed to pass through a flow path connected through the branching portion, the drug solution flows so as to push any air inside the branching portion to the downstream side of the flow path. Therefore, before supplying the drug solution to the inside of the patient's body, the air inside the flow path can be discharged together with a small amount of the drug solution, and the flow path can be filled with the drug solution without any air. Consequently, air is prevented from entering the body when the drug solution is administered to the body. Similarly, when the flow path of the branching portion is connected to the chamber, any air inside the branching portion and chamber can be expelled from the flow path of the branching portion with the drug solution being supplied, and subsequently, the drug solution can be supplied to the body.

Another characteristic of the liquid-mixing infusor of this disclosure with respect to its configuration is that the chamber may be formed as a based cylinder open at the top and closed at the bottom, the operation portion being formed as a cap-shaped body attached rotatably on the top end opening side of the chamber and a branching portion being installed inside the operation portion.

Accordingly, the bottom of the chamber can be formed as a flat surface; consequently, for example, it is possible to install a plurality of liquid-mixing infusors on an installation plate, and each liquid-mixing infusor may have a plurality of infusion tubes connected. With this set up, it is possible to feed a large number of drug solutions to the body concomitantly. In addition, by installing the liquid-mixing infusor on an installation plate, the operation of the operation portion can be carried out easily with a single hand. Moreover, the operation part is positioned at the top of each liquid-mixing infusor; consequently, it is easy to see, and the operation position of the rotary portion can be easily confirmed. Furthermore, the cap-shaped body may be installed directly on the top end opening of the chamber, or it may be installed on the top end opening through a part such as valve. This cap-like body may be a shape close to a cylinder.

Yet another characteristic of the liquid-mixing infusor of this disclosure is that the chamber is formed as a cylinder with both ends open, an operation portion is allowed to extend to the outside of the chamber from the bottom opening of the chamber, at the same time, a cap-shaped body is attached at the top opening of the chamber, and the branching portion is installed inside the cap-shaped body. Furthermore, in this case, the operation portion is preferably made movable along a portion of a specified range at the periphery of the bottom opening of the chamber, and the portion of the operation portion outside the movement range is preferably extended downward beyond the bottom end of the operation portion.

Accordingly, the branching portion positioned at the upper portion of the liquid-mixing infusor can be held in a fixed state against the chamber, and, consequently, it is possible to stabilize the flow path formed on the side of the branching portion. Furthermore, by installing an extension at the bottom opening of the chamber, it is possible to attach the liquid-mixing infusor to an installation part when it is extended. As a result, the operation portion does not cause any interference at the time of installation of the liquid-mixing infusor on an installation part, and at the same time, the operation when the liquid-mixing infusor is installed on the installation part becomes easy.

Still another characteristic of the liquid-mixing infusor of this disclosure is that the valve has a pair of blocking sections blocking in a specific direction between the pair of branch tubes and the chamber when the valve is installed inside the chamber, and pair of depressed sections for connecting between the pair of branch tubes and the chamber when the valve is allowed to rotate about 90° from the specific direction; and furthermore, the widths of the pair of depressed portions along the rotational direction are set to be different, allowing only one of the pair of branch tubes to be connected to the chamber when the valve is allowed to rotate by a specific angle smaller than about 90° from the specific direction.

In this case, it is possible to configure the valve, for example, by installing a pair of depressed connecting sections having different sizes in the width direction for connection between the pair of branch tubes and the chamber on both sides with the central axis between them in the cylinder, allowing the unchanged other portions of the cylinder to form a pair of blocking sections blocking the pair of branch tubes and chamber, respectively. Furthermore, the pair of depressed connecting sections can be connected through the branching portion. In addition, the size difference in this case between the pair of the depressed connecting sections is set so that the small depressed connecting section is allowed to be movable with one branch tube and the chamber connected within the range in which the large depressed connecting section is movable with the other branch tube and chamber being connected. Accordingly, it is possible to carry out flow path switching reliably with a simple structure.

Furthermore, still another characteristic of the liquid-mixing infusor of this disclosure is that the valve has a pair of blocking sections blocking in a specific direction between the pair of branch tubes and the chamber when the valve is installed inside the chamber, and a pair of depressed sections connecting between the pair of branch tubes and the chamber when the valve is allowed to rotate about 90° from the specific direction; and furthermore, the positions of the pair of depressed connecting sections are shifted from the portions of the outer circumference of the valve crossing the hypothetical line perpendicular to the central axis of the valve, allowing only one of the pair of branch tubes to be connected to the chamber when the valve is allowed to rotate by a specific angle smaller than about 90° from the specific direction.

In this case, for example, the portions facing the opening of the pair of branch tubes at the pair of depressed connecting sections are allowed to be larger than the openings of the pair of branch tubes, and at the same time, the positions of the depressed connecting sections are allowed to be displaced from two sides at the periphery of the valve with the central axis of the valve in between. Furthermore, the widths of the pair of depressed connecting sections along the rotational direction are set to be identical, and when the front edge portion of one depressed connecting portion faces the opening of one branch tube, and this depressed connecting portion is connected to this branch tube, the front end portion of the other depressed connecting portion faces the opening of the other branch tube, and the other depressed connecting portion is connected to the other branch tube.

Accordingly, a depressed connecting section is blocked when the valve is rotated so that the rear edge side of the other depressed connecting section faces the opening of a branch tube connecting the depressed connecting section to the branch tube. Furthermore, the other depressed connecting section described above continues to be connected to the other branch tube by rotating the valve so that the rear edge portion of the above other depressed section faces the opening of the other branch tube, and the depressed section described above is blocked. As a result, it is also possible to switch the flow path reliably with a simple structure.

Furthermore, by setting the widths of pair of the depressed connecting sections to be different, it is also possible to allow only one of the pair of depressed connecting sections or both to be connected to the chamber or block both by suitably adjusting the position relation of the pair of branch tubes and openings. Incidentally, the fact that the positions of the pair of depressed connecting sections are shifted in this case from the portions of the outer circumference of the valve crossing a hypothetical line means that when the center of one depressed connecting portion along the circumferential direction is on a hypothetical line perpendicular to the central axis of the valve, the center of the other depressed connecting section is not positioned on a hypothetical line perpendicular to the central axis of the valve.

Moreover, another characteristic of the liquid-mixing infusor of this disclosure is that the circumferential surface of the chamber has positioning bosses installed, and at the same time, the operation portion has stops installed to stop the valve at a specified position by allowing it to be engaged with the positioning bosses. Accordingly, the rotary portion can be reliably stopped at the specified position allowing the valve to carry out flow path switching accurately.

Finally, still another characteristic of the liquid-mixing infusor of this disclosure is that the branching portion is allowed to include roughly cylindrical branch tubes installed on the top opening side of the chamber, and rubber plugs which are installed inside the branch tubes and capable of allowing insertion tubes to pass through. Accordingly, the flow path of the branching portion formed above the chamber can be connected to or blocked from the inside of the chamber by a simple method. Furthermore, as an insertion tube in this case, it is possible to use a connector insertion portion, male luer of a connector or syringe or needle such as needle for injection, dull needle, Furthermore, if the tip of such an insertion tube is not sharp, the rubber stopper may have a slit for inserting an insertion tube.

BRIEF DESCRIPTION OF DRAWINGS

The present disclosure will be explained by way of example only with reference to the accompanying drawings in which.

DETAILED DESCRIPTION

Figure 1:
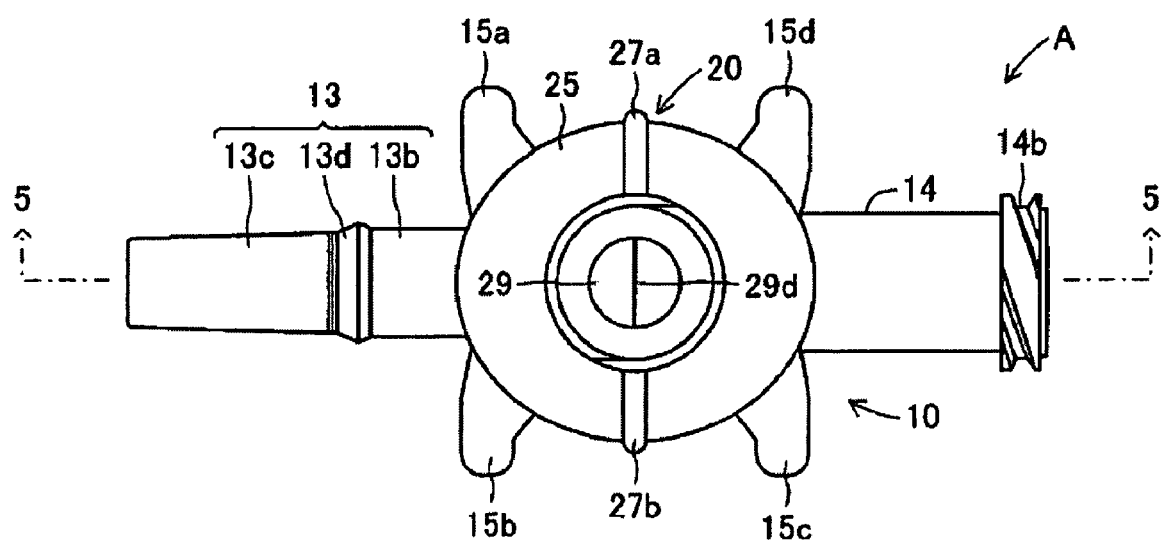
FIG. 1 is a plan view of a liquid-mixing infusor of the first embodiment of this disclosure.
Figure 2:
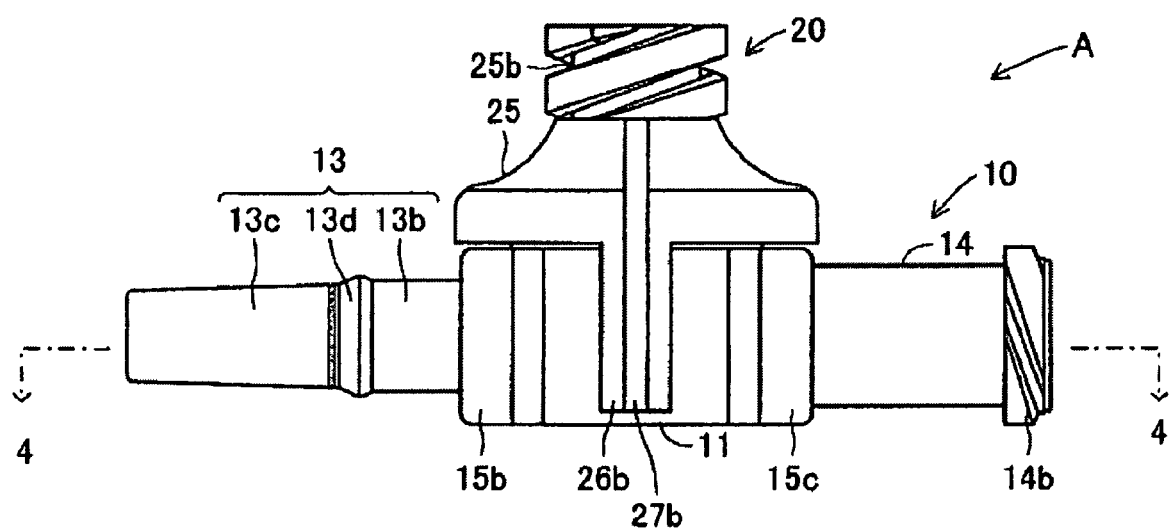
FIG. 2 is a side view of the liquid-mixing infusor of the first embodiment.
Figure 3:
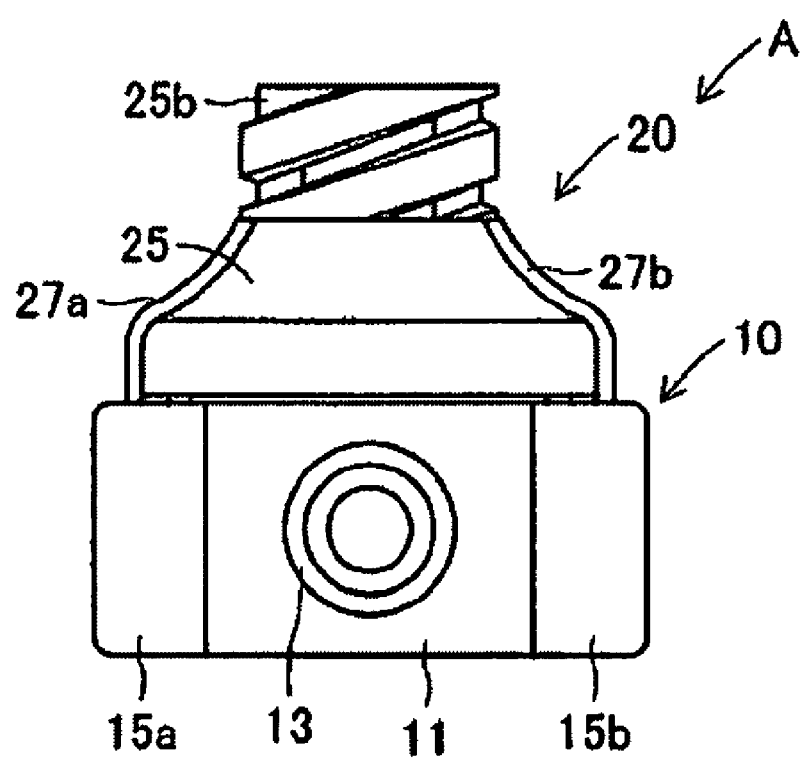
FIG. 3 is a front view of the liquid-mixing infusor of the first embodiment.

A liquid-mixing infusor as the first embodiment of this disclosure is explained in detail by using drawings as follows. FIGS. 1-3 are drawings showing a liquid-mixing infusor A of this embodiment, and this liquid-mixing infusor A includes a liquid-mixing infusor main body 10 and rotary portion 20. The liquid-mixing infusor main body 10 includes a chamber 11 formed as a cylinder having a short length in the axial direction and vertically disposed axial direction, confluent branching portion 12 formed above the chamber 11 (see FIG. 5) and a pair of downstream and upstream branch tubes 13 and 14, respectively connected to two sides of the chamber 11 at its peripheral surface and extended coaxially maintaining an angle of 180°.

Figure 4:
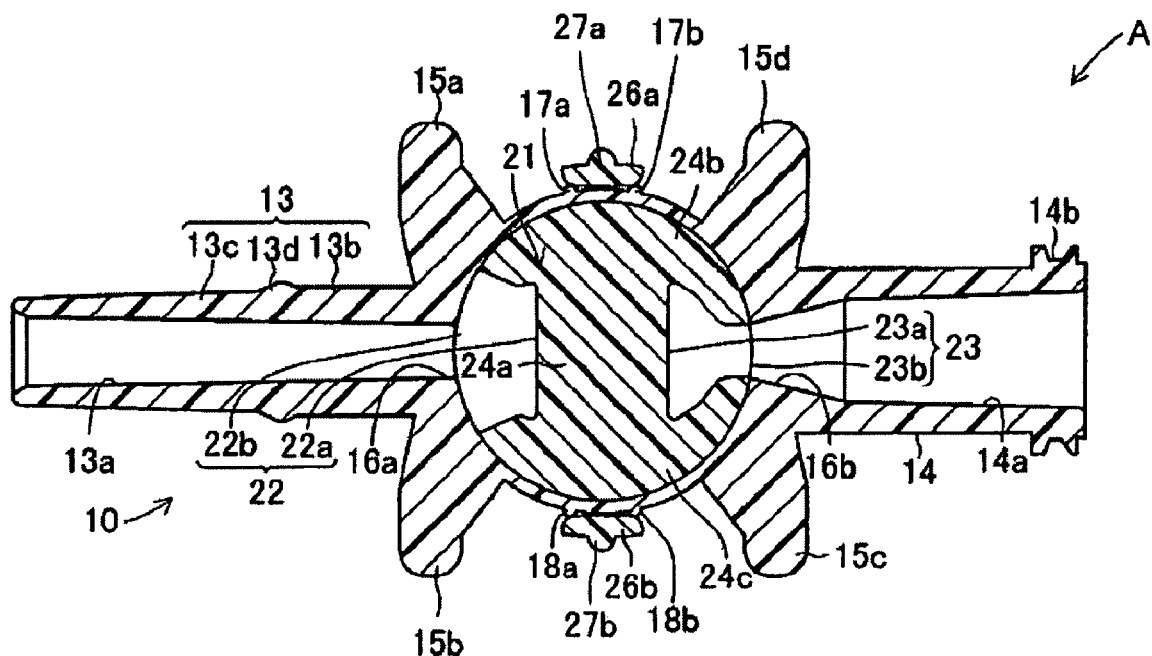
FIG. 4 is a cross section of FIG. 2 along the line 4-4.
Figure 5:
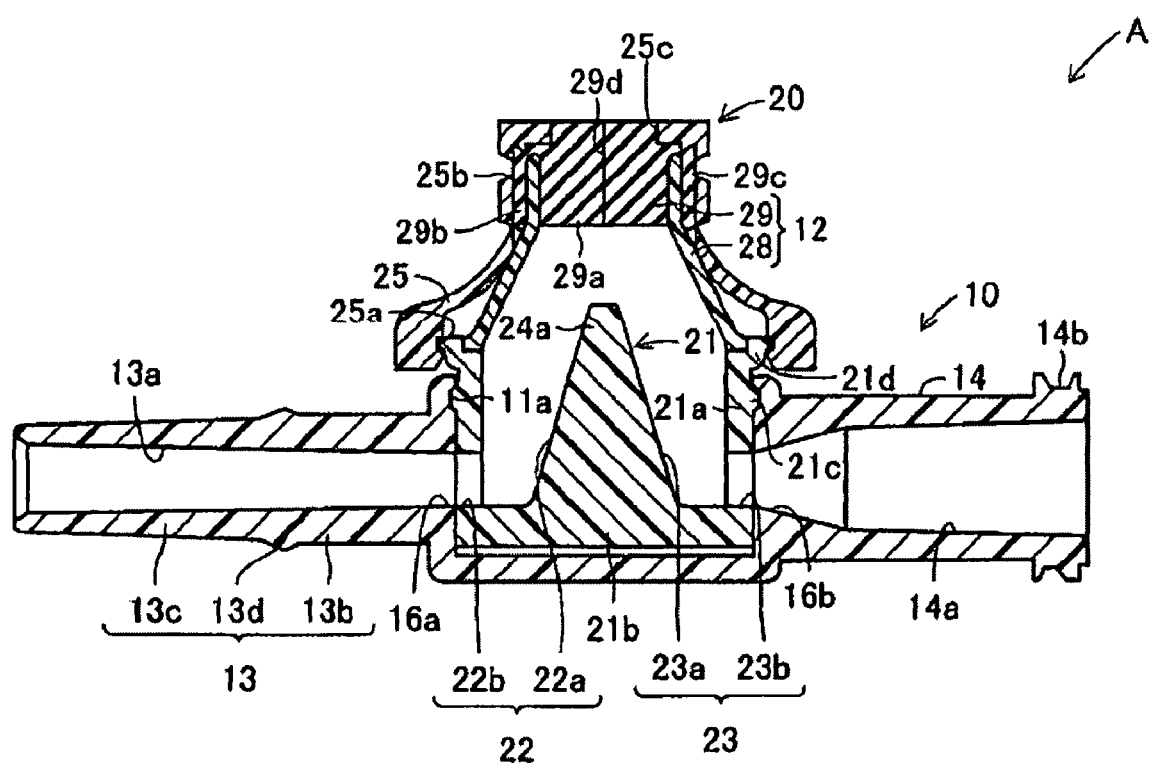
FIG. 5 is a cross section of FIG. 1 along the line 5-5.

The main portion of the chamber 11 forms a bottomed cylinder with its bottom closed and top open, and on its peripheral surface in the circumferential direction, handling extrusions 15a, 15b, 15c and 15d are formed. The handling extrusions 15a, 15b, 15c and 15d extend from the peripheral surface of the chamber in four directions, and their tips extend in external directions perpendicular to the axial directions of the downstream branch tube 13 and upstream branch tube 14. As shown in FIG. 4 and FIG. 5, the portions facing each other at about the center of the axial direction of the chamber 11 have two connection holes 16a and 16b, respectively.

A connection hole 16a is formed between the handling extrusions 15a and 15b, and a connection hole 16b is formed between the handling extrusions 15c and 15d. The portion of the chamber 11 corresponding to the connection hole 16a has the downstream branch tube 13 installed, and through the connection hole 16a, the inside of the chamber 11 and flow path 13a formed inside the downstream branch tube 13 are connected. Furthermore, the portion of the chamber 11 corresponding to the connection hole 16b has the upstream branch tube 14 installed, and through the connection hole 16b, the inside of the chamber 11 and flow path 14a formed inside the upstream branch tube 14 are connected.

The downstream branch tube 13 is formed together with the chamber 11 as a single body, and it includes a base end 13b positioned on the side of the chamber 11 and male luer 13c positioned on the tip side and made thinner than the base end 13b. The male luer 13c is formed tapered towards the tip end side from the side of the base end 13b. In the border between the base end 13b and male luer 13c on the circumferential surface of the downstream branch tube 13, an extrusion 13d is formed along the circumference.

Moreover, the upstream branch tube 14 is formed integrally with the chamber 11. The downstream side of a flow path 14a formed inside (side of the chamber 11) is formed tapered with the diameter on the side of the connection hole 16b set small but increasing as it moves away from the connection hole 16b. Furthermore, the upstream side of the flow path 14a is formed also tapered with a gradually increasing diameter as it approaches the opening of the upstream branch tube 14. At the circumference of the opening of the upstream branch tube 14, a screw for connection 14b is formed. On the peripheral surface of the chamber 11 between the handling extrusions 15a and 15d, small positioning bosses 17a and 17b extending in the vertical direction are formed with spacing so as to partition the distance between the handling extrusions 15a and 15d into three equal portions.

Similarly, on the peripheral surface of the chamber 11 between the handling extrusions 15b and 15c, small positioning bosses 18a and 18b extending in the vertical direction are formed with spacing so as to partition the distance between the handling extrusions 15b and 15c into three equal portions. Furthermore, on the top end portion of the inner circumferential surface of the chamber 11, an annular catch 11a for a depressed portion is formed, and the rotary portion 20 is installed in a freely rotatable manner on this catch 11a. Incidentally, the confluent branching portion 12 constitutes a portion of the liquid-mixing infusor of main body 10, but as explained later, it is incorporated in the rotary portion 20.

The rotary portion 20 includes a valve 21 and an operation portion 25 connected to the top end of the valve 21. The valve 21 is installed inside the chamber 11, and by operating the operation portion 25, it is rotatable in the periaxial direction inside the chamber 11. The outer shape of this valve 21 is formed in an approximately cylindrical shape. The two sides of the cylinder with its axis in between have depressed connecting sections 22 and 23 formed extending from the top to the bottom side of the lateral surface. The depressed connecting section 22 includes a top depression 22a consisting of the top side and connection hole 22b penetrating through a portion between the bottom of the top depression 22a and peripheral surface of the valve 21.

In the case of peripheral surface of the top depression 22a, the plane positioned on the outer peripheral side of the valve 21 is formed on the arc-shaped curvature along the peripheral surface of the valve 21, and the surface positioned at the middle side of the valve 21 is formed as a conical surface with the top end being close to the center of the valve 21 but coming away from the center of the valve 21 downwards. In addition, the width of the connection hole 22b along the circumferential direction is set to be slightly larger than three times the diameter of the connection hole 16a, and the vertical length of the connection hole 22b is set about the same as the diameter of the connection hole 16a.

Furthermore, the depressed connecting section 23 includes a top depression 23a consisting of the top side and connection hole 23b penetrating through a portion between the bottom of the top depression 23a and peripheral surface of the valve 21. In the case of peripheral surface of the top depression 23a, the surface positioned on the outer peripheral side of the valve 21 is formed on the arc-shaped curvature along the peripheral surface of the valve 21, and the surface positioned at the middle side of the valve 21 is formed as a conical surface with the top end being close to the center of the valve 21 but coming away from the center of the valve 21 downwards. In addition, the diameter of the connection hole 23b is set about same as that of the connection hole 16b.

Therefore, a vertical wall 24a with conical surface on both sides is formed extending in the radial direction between the depressed connecting sections 22 and 23 in the valve 21, and at the two sides of this vertical wall 24a, a pair of blocking sections 24b and 24c constituting a portion of the periphery 21a of the valve 21 are formed. Namely, the valve 21 includes the vertical wall 24a, a pair of blocking sections 24b and 24c, peripheral side 21a and plane bottom 21b, and if the connection hole 23b is allowed to match with the connection hole 16b, the flow path 14a of the upstream branch tube 14 and the inside of the chamber 11 (space between the chamber 11 and valve 21) are connected. In this case, the connection hole 16a is positioned at the center portion in the width direction of the connection hole 22b, and the inside of the chamber 11 and the flow path 13a of the downstream branch tube 13 are connected.

Consequently, the upstream branch tube 14 and downstream branch tube 13 are connected through the chamber 11, and if a drug solution is injected into the flow path 14a of the upstream branch tube 14, the drug solution accumulates in the depressed connecting section 23. Subsequently, when the liquid level of the drug solution is above the top end of the vertical wall 24a, the solution flows to the depressed connecting section 22 and to the flow path 13a of the downstream branch tube 13 though the connection hole 22b. In this case, the back flow of the drug solution is prevented by the vertical wall 24a, and at the same time, the drug solution is allowed to pass through the top portion of the chamber 11 preventing any air from accumulating inside the chamber 11.

Figure 6:
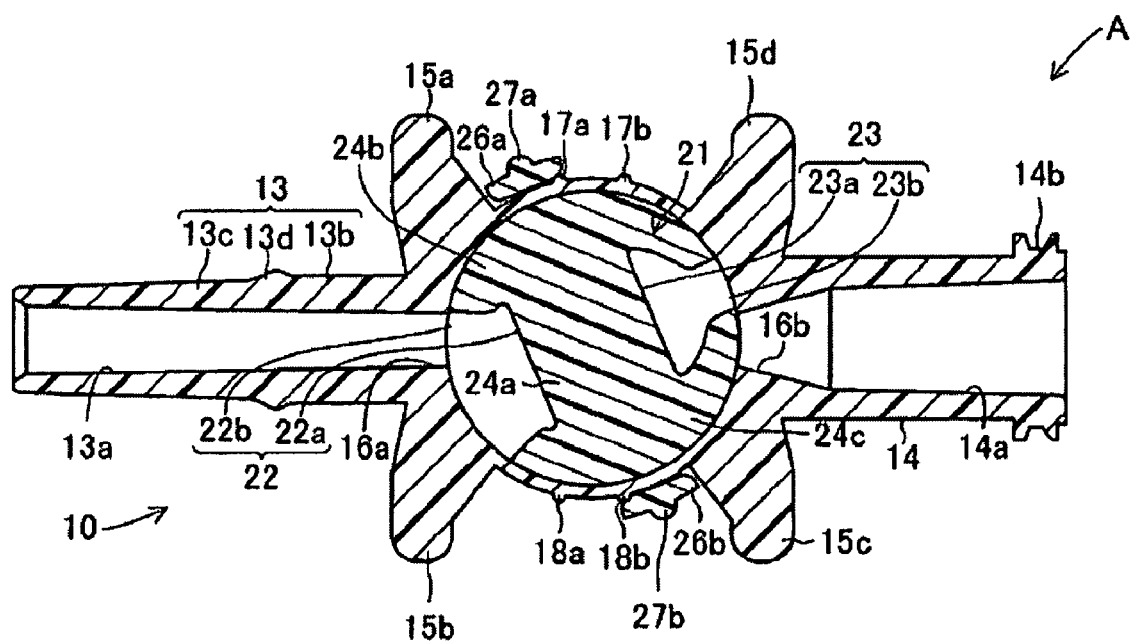
FIG. 6 is a cross section showing the liquid-mixing infusor in a state of the valve rotated in the counterclockwise direction.
Figure 7:
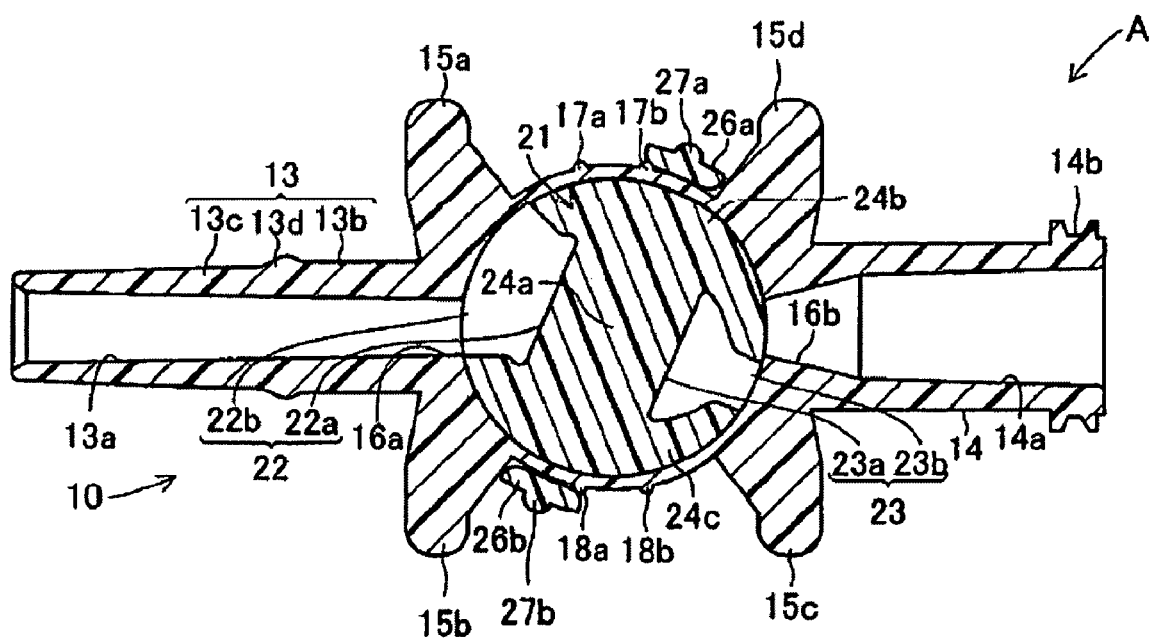
FIG. 7 is a cross section showing the liquid-mixing infusor in a state of the valve rotated in the clockwise direction.

Furthermore, as shown in the plan view of FIG. 6, the valve 21 is allowed to rotate by a specific angle in the counterclockwise direction from the state shown in FIG. 4, thus, one end portion in the width direction of the connection hole 22b is positioned at one end portion of the connection hole 16a while sustaining the state of connection between the connection hole 22b and connection hole 16a, and the connection hole 16b is blocked by the blocking section 24c. Consequently, the chamber 11 and downstream branch tube 13 are connected, and the upstream branch tube 14 and chamber 11 are blocked. Similarly as shown in FIG. 7, the valve 21 is allowed to rotate by a specific angle in the clockwise direction from the state of FIG. 4, thus, the other end portion in the width direction of the connection hole 22b is positioned at the other end of the connection hole 16a while sustaining the state of connection between the connection hole 22b and connection hole 16a, and the connection hole 16b is blocked by the blocking section 24b.

Therefore, chamber 11 and downstream branch tube 13 are connected, and the upstream branch tube 14 and chamber 11 are blocked. Furthermore, although not shown in the figures, the connection holes 16a or 16b can be blocked with the blocking sections 24b or 24c by allowing the valve 21 to rotate in the counterclockwise direction from the state of FIG. 6 or allowing the valve 21 to rotate in the clockwise direction from the state of FIG. 7. As a result, both upstream branch tube 14 and chamber 11 and downstream branch tube 13 and chamber 11 can be blocked.

The top end portion of the valve 21 has a catch portion 21c allowed it to be engaged with the catch 11a of the chamber 11 rotatably formed along the circumference, and the valve 21 is rotatable against the chamber 11 when catching portion 21c is engaged with the catch 11a. The top peripheral portion of the valve 21 is formed at a catch part 21d extruded outwards, the inside of which is a catching depression, and the outside of which is a catching extrusion.

The operation portion 25 is installed at the upper circumference of the valve 21, and together with the valve 21, it is rotatable against the chamber 11. This operation portion 25 includes a part separate from the valve 21, and it is configured as a tapered cylinder (cap-shaped body) with the diameter gradually reduced upwards from the side of the valve 21. Furthermore, in a plan view, operation portion 25 has an oval shape. At the bottom end of the inner peripheral surface, operation portion 25 has a catch portion 25a formed, and this catch portion 25a is allowed to engage with the catch portion 21c of the valve 21 connecting the operation portion 25 to the valve 21.

Moreover, a pair of thin plate-shaped stops 26a and 26b extends downwards from two ends along the axle of the oval at the bottom circumferential portion of the operation portion 25. The stop 26a is movably configured along the peripheral surface of the chamber 11 between the handling extrusions 15a and 15b and stoppable between the handling extrusion 15a and positioning boss 17a, positioning bosses 17a and 17b, and positioning boss 17b and handling extrusion 15d, respectively. Furthermore, together with the movement or stopping of the stop 26a, the stop 26b is moved along the peripheral surface of the chamber 11 between the handling extrusions 15b and 15c or stopped between the handling extrusion 15b and positioning boss 18a, positioning bosses 18a and 18b, and positioning boss 18b and handling extrusion 15c, respectively.

Figure 8:
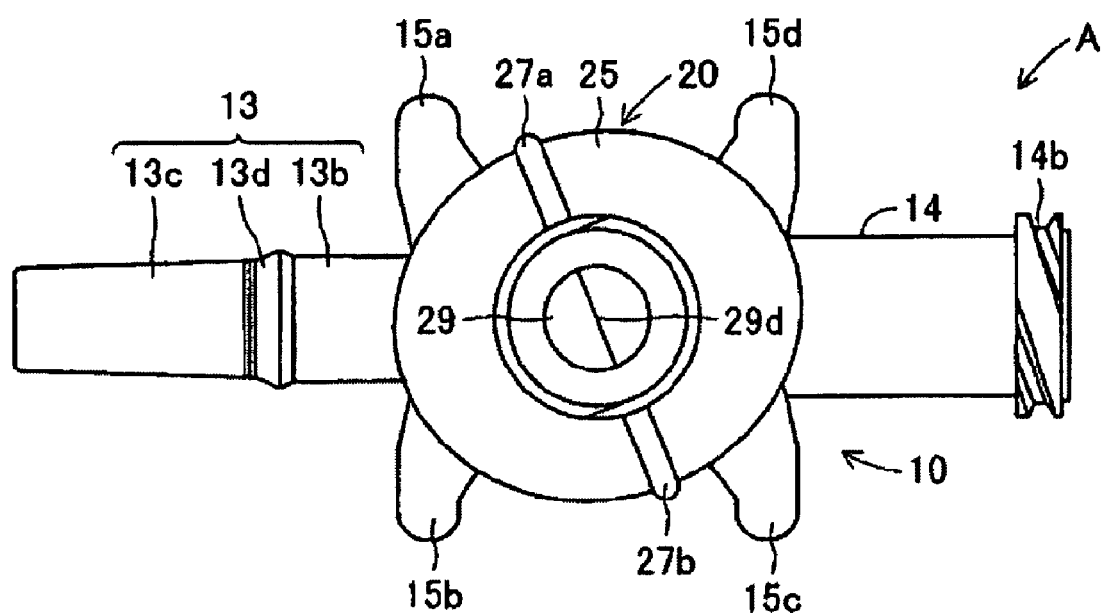
FIG. 8 is a plan view showing the liquid-mixing infusor in a state of the operation portion rotated in the counterclockwise direction.
Figure 9:
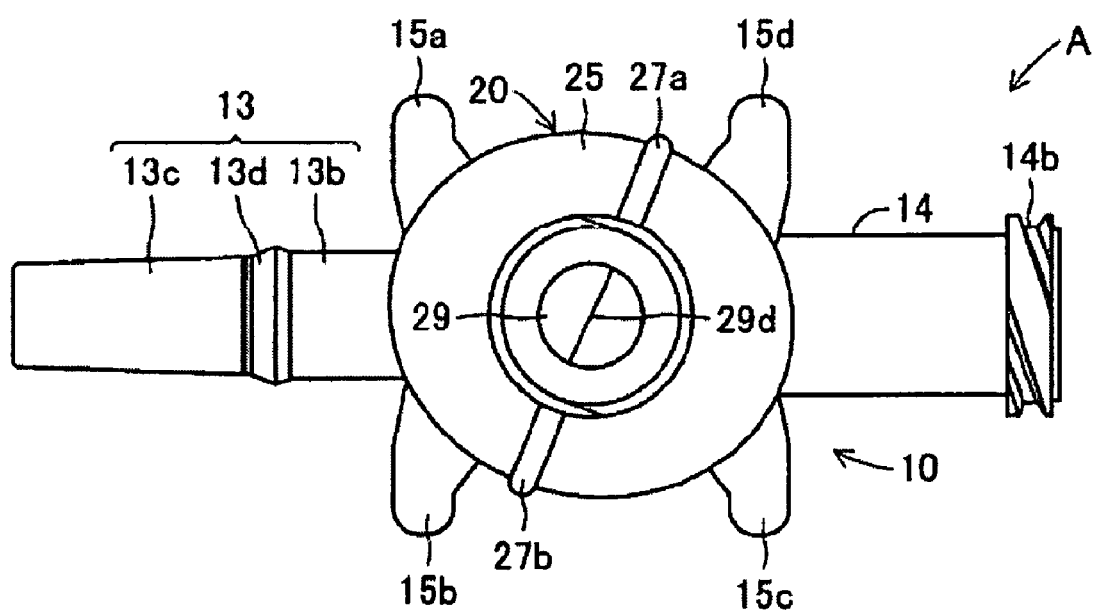
FIG. 9 is a plan view showing the liquid-mixing infusor in a state of the operation portion rotated in the clockwise direction.

A linear extrusion 27a is formed from the bottom center on the surface of the stop 26a to the upper surface of the operation portion 25, and a line extrusion 27b is formed from the bottom center on the surface of the stop 26b to the upper surface of the operation portion 25. As shown in FIGS. 8 and 9 these line extrusions 27a and 27b are used to confirm the position from the top when the operation portion 25 is used for rotation. Furthermore, the position of the operation portion 25 in the periaxial direction is confirmed by using the stops 26a and 26b and line extrusions 27a and 27b and by inspection from the side of the liquid-mixing infusor A.

The positions of the line extrusions 27a and 27b in a plan view are set positions along the length direction passing the center in the width direction of the vertical wall 24a of the valve 21. Therefore, the periaxial position of the valve 21 can be confirmed also from the positions of the line extrusions 27a and 27b. FIG. 6 shows the valve 21 inside the liquid-mixing infusor main body 10 when the line extrusions 27a and 27b take the positions shown in FIG. 8, and FIG. 7 shows the valve 21 inside the liquid-mixing infusor main body 10 when the linear extrusions 27a and 27b take the positions shown in FIG. 9. Furthermore, FIG. 4 shows the valve 21 inside the liquid-mixing infusor main body 10 when the linear extrusions 27a and 27b take the positions shown in FIG. 1. The top portion of the operation portion 25 is formed cylindrical, and its peripheral surface has a thread 25b formed. In addition, the top end plane of the operation portion 25 has an opening 25c installed at its center.

The confluent branching portion 12 includes a confluent branch tube 28 roughly cylindrical in shape installed inside the operation portion 25 and rubber stopper 29 made of natural or synthetic rubber and installed at the top opening of the confluent branch tube 28. The confluent branch tube 28 is a short cylinder tapered upwards with the diameter gradually reduced, and it is fixed on the valve 21 by engagement with the inner side catch recess at the catching part 21d of the valve 21. Furthermore, the outer diameter of the top of the confluent branch tube 28 is slightly smaller than the inner diameter of the top portion of the operation portion 25.

The rubber stopper 29 includes a thick disc-shaped stopper main body 29a and belt-shaped attachment pieces 29b and 29c extending from the two upper sides of the stopper main body 29a. The stopper main body 29a is pushed into the confluent branch tube 28 from the top opening of the confluent branch tube 28, and the rubber stopper 29 is fixed by fixing the operation portion 25 at the outside of the confluent branch tube 28 with attachment pieces 29b and 29c set along the peripheral surface of the confluent branch tube 28. Namely, the operation portion 25 is fixed by pressing the attachment pieces 29b and 29c against the side of the confluent branch tube 28, and at the same time, the peripheral portion of the top surface of the stopper main body 29a is pressed also against the confluent branch tube 28, preventing the stop from coming off.

Furthermore, this rubber stopper 29 has a slit 29d installed forming a flow path of the confluent branching portion 12 passing through the inner side of the confluent branch tube 28 and outer side of the confluent branch tube 28. this slit 29d is in its closed state because of the elastic force of the rubber stopper 29 when the flow path of the confluent branching portion 12 is not used. Furthermore, if the flow path of the confluent branching portion 12 is used, a suitable connector (not shown in the figures) is inserted into the slit 29d to form a flow path. This connector is equipped with a male luer with a flow path formed inside, and this male luer is inserted into the slit 29d of the rubber stopper 29 to connect the connector and inside of the confluent branch tube 28. Furthermore, in this case, the peripheral surface of the male luer comes into close contact with the inner surface of the slit 29d because of the elasticity of the rubber stopper 29.

When administering a required drug solution to a patient (not shown) with this configuration, the rear end portion of an infusion tube (not shown) with an attached needle remaining inserted in the patient is connected to the downstream branch tube 13. On the other side, a male luer attached to the end of an infusion tube extended from a container containing the drug solution to be administered to the patient is connected to the upstream branch tube 14. With the indwelling needle attached to the body, the operation portion 25 is operated sending the drug solution from the container to the patient to administer the drug solution to the patient. Furthermore, if another drug solution is to be administered to the patient in addition to the drug solution administer from the container, this other drug solution is injected into the chamber 11 from the confluent branching portion 12 through an infusion tube connected to a connector.

Namely, if the operation portion 25 is operated with the connector attached to the confluent branching portion 12 to obtain the state shown in FIG. 8 or FIG. 9, the connector and downstream branch tube 13 are connected inside the chamber 11 through the recessed connecting portion 22. In this case, the blocking section 24c or 24b of the valve 21 blocks the connection hole 16b, and as a result, the upstream branch tube 14 is blocked against the inside of the chamber 11. This state can be confirmed by observing the positions of the strip extrusions 27a and 27b preventing the occurrence of any erroneous operation. Furthermore, the stop 26a is stopped in at a position between the handling extrusion 15a and positioning boss 17a or positioning both 17b and handling extrusion 15d, and at the same time, the stop 26b is stopped at a position between the positioning boss 18b and handling extrusion 15c or handling extrusion 15b and positioning boss 18a. Consequently, the rotary portion 20 is reliably fixed on the prescribed position.

If the operation portion 25 is operated to achieve the state shown in FIG. 1 and FIG. 2, the connector, downstream branch tube 13 and upstream branch tube 14, are respectively connected through the chamber 11. In this case, as shown in FIG. 4, the stop 26a is stopped at a position between the positioning bosses 17a and 17b, and the stop 26b is stopped at a position between the positioning bosses 18a and 18b. Consequently, the rotary portion 20 is reliably fixed at a prescribed position. Furthermore, before inserting and leaving the indwelling needle in the patient, a small amount of the drug solution is discharged from the tip of the needle. As a result, any air present in the flow path together with the drug solution can be expelled. Furthermore, the liquid-mixing infusor A may be attached to an installation board, before using it.

As described above, the liquid-mixing infusor A of this embodiment is equipped with the valve 21 rotatable in the periaxial direction inside the chamber 11 and operation portion 25 connected to the valve 21 and positioned above the chamber 11. When the operation portion 25 is allowed to be rotated in an optional direction to achieve the state shown in FIG. 1, FIG. 8 or FIG. 9, the valve 21 allows the connection or blocking section among the downstream branch tube 13, upstream branch tube 14 and chamber 11, respectively. Therefore, the opening and closing operations among the downstream branch tube 13, upstream branch tube 14 and chamber 11 can be carried out conveniently, and at the same time, the operation can be carried out easily with a single hand. Furthermore, by inserting a connector into the rubber stopper 29 of the confluent branching portion 12, it is possible to connect the connector to the downstream branch tube 13 and upstream branch tube 14 or to the downstream branch tube 13. As a result, it becomes possible to provide a patient with one or two kinds of drug solutions.

If the drug solution is allowed to flow from the upstream branch tube 14 to the downstream branch tube 13, the drug solution is accumulated once inside the recess 23 for connection, subsequently flows to the side of the recess 22 for connection by going over the top end of the vertical wall 24a and to the flow path 13a of the downstream branch tube 13 through the connection hole 22b. In this case, the vertical wall 24a prevents the drug solution from back-flow, and at the same time, by allowing the drug solution to pass through the upper portion of the chamber 11, prevents any air from accumulating inside the chamber 11. Therefore, the drug solution is properly administered to the patient.

Since the bottom of the chamber 11 is formed as a flat plane, it is possible to install a plurality of liquid-mixing infusors A on an installation plate, and a plurality of infusion tubes may be connected to each liquid-mixing infusor A. Accordingly, it is possible to feed a plurality of drug solutions concomitantly into the body. Furthermore, if the liquid-mixing infusor A is installed on an installation plate, the operation portion 25 can be operated easily with a single hand. In addition, the operation portion 25 is positioned at the top portion of the liquid-mixing infusor A, it is easily visible, and the operating position of the valve 21 can be easily confirmed.

Furthermore, the peripheral surface of the chamber 11 has positioning bosses 17a, installed, and at the same time, the operation portion 25 can be equipped with the stops 26a and 26b. As a result, the rotary portion 20 can be reliably stopped at a prescribed position enabling accurate flow path switching by the valve 21. In addition, any undesired movement of the rotary portion 20 switching the flow path is effectively prevented. The stops 26a and 26b have corresponding strip extrusions 27a and 27b, respectively reducing the chance of the operator making any erroneous operation to connect or block an incorrect flow path. In addition, the confluent branching portion is allowed to include the confluent branch tube 28 and rubber stopper 29 equipped with the slit 29d, and consequently, the flow path of the confluent branching portion 12 formed at the top portion of the chamber 11 can be connected to or blocked against the inside of the chamber 11 with simple procedures.

Figure 10:
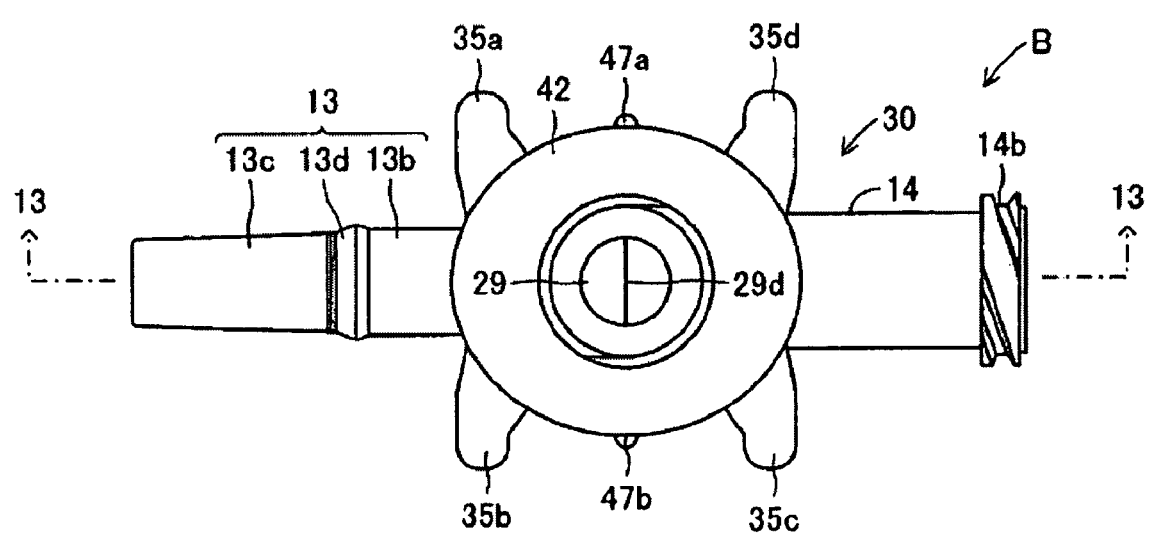
FIG. 10 is a plan view of a liquid-mixing infusor of the second embodiment of this disclosure.
Figure 11:
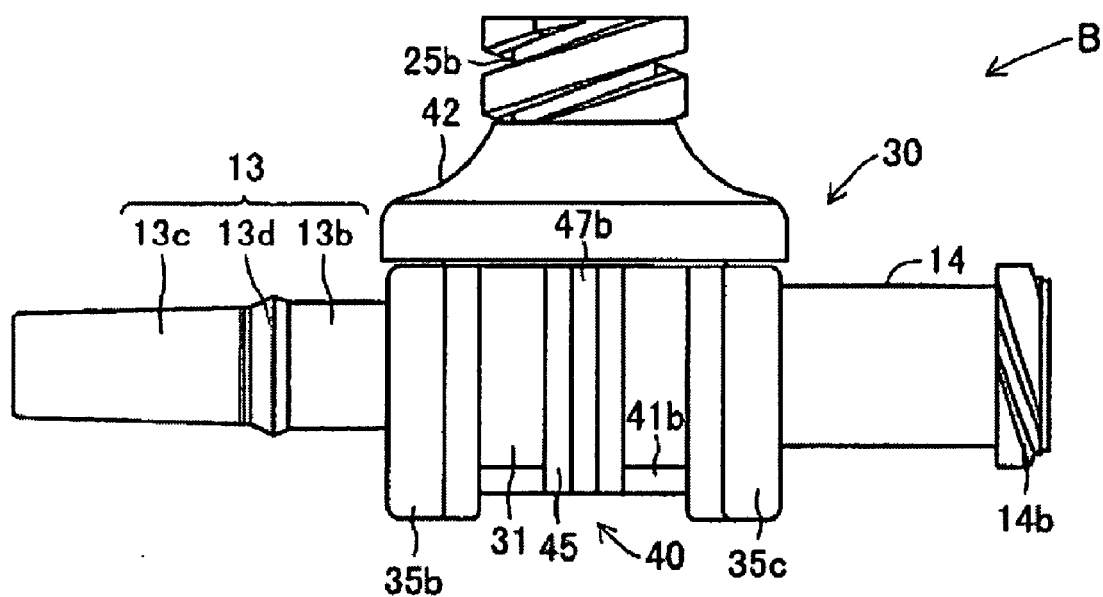
FIG. 11 is a front view of the liquid-mixing infusor of the second embodiment.
Figure 12:
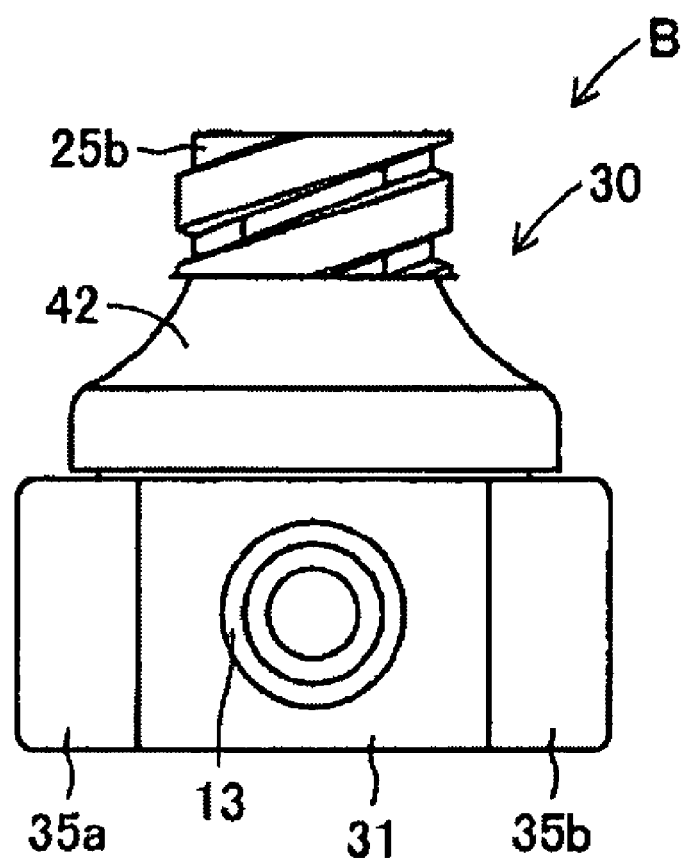
FIG. 12 is a side view of the liquid-mixing infusor of the second embodiment.
Figure 13:
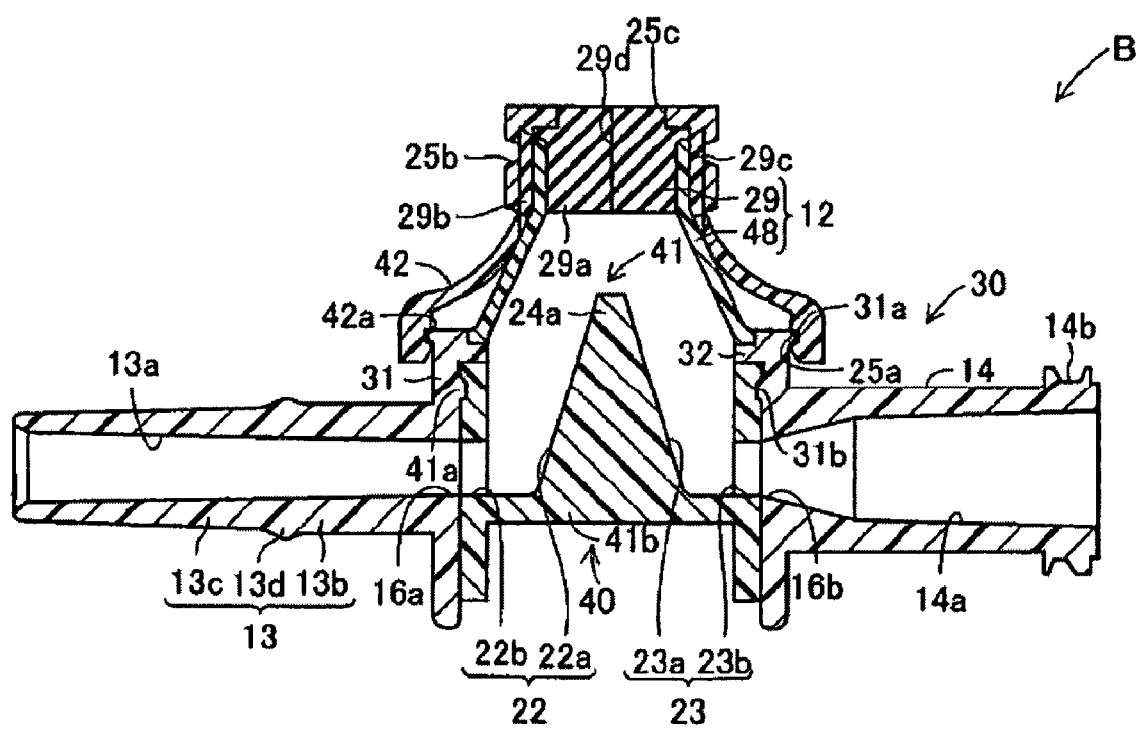
FIG. 13 is a cross section of FIG. 10 along the line 13-13.

FIG. 10-FIG. 12 shows a liquid-mixing infusor B of the second embodiment of this disclosure. This liquid-mixing infusor B includes a liquid-mixing infusor main body 30 and rotary portion 40. The liquid-mixing infusor main body 30 has a chamber 31, which is a cylinder with top and bottom ends opened as shown in FIG. 13. The top end periphery of the chamber 31 has an annular catch 31a including an extrusion, and at a position slightly lower than this, catch 31a is on the inner circumferential surface of the chamber 31, and a ring shaped extrusion 32 protruding inwards is formed.

Below this extrusion 32 formed on the inner circumferential surface of the chamber 31, an annular catch 31b including an extrusion is formed, and the rotary portion 40 is installed so as to be freely rotatable on this catch 31b. Furthermore, the outer periphery of the main body portion of the chamber 31 has handling extrusions 35a, 35b, 35c and 35d formed with spacing between them in the circumferential direction. These handling extrusions 35a, 35b, 35c and 35d extend downwards from the main body portion of the chamber 31, and thus they are longer in the vertical direction than the handling extrusions 15a, 15b, 15c and 15d described above for the first embodiment. Furthermore, the bottom end portions of the section between the handling extrusions 15a and 15b and handling extrusions 15c and 15d are extended to the same position as the bottom ends of the handling extrusions 15a, 15b, 15c and 15d.

The rotary portion 40 includes a valve 41 and pair of operation portions 45 (only one operation portion 45 shown in the figure) connected to the bottom end portion of the valve 41. The top end portion at the peripheral plane of the valve 41 has a catching portion 41a formed along the circumference including a recess engaged with the catch 31b of the chamber 31 in a rotatable state, and the valve 41 is rotatable against the chamber 31 with the catching portion 41a allowed to engage with the catch 31b. Furthermore, the top end of the valve 41 comes into close contact in a liquid-tight manner with the bottom surface of the extrusion 32 of the chamber 31.

Furthermore, the operation portions 45 include respectively thin plates extending upwards along the peripheral surface of the chamber 31 from both sides of the circumference of the bottom surface 41b of the valve 41. At the center portions in the width direction on the surface of the pair of the operation portions 45, strip extrusions 47a and 47b extending vertically are respectively formed. Namely, the operation portions 45 are used to carry out a rotary operation of the valve 41, and at the same time, acts as steps restricting the rotary angle of the rotary portion 40 similarly to the stops 26a and 26b described above for the first embodiment.

Furthermore, the upper periphery of the chamber 31 has a cap 42 having roughly the same structure as that of the operation portion 25 in the above embodiment attached. The inner circumferential lower end of this cap 42 has a catching portion 42a including a recess engageable with the catch 31a formed, and the cap 42 is fixed on the chamber 31 by allowing the catching portion 42a to engage with the catch 31a. Furthermore, a confluent branch tube 48 is attached to the chamber 31 with the end allowed to engage with the top plane of the extrusion 32 and inner circumferential plane of the chamber 31. The configurations of other parts in chamber 31 of this liquid-mixing infusor B are the same as those in the liquid-mixing infusor A described above for the first embodiment. Therefore, the same numerals are used for the same parts and any further explanations are omitted.

To administer a specific drug solution to the patient with this configuration, the downstream branch tube 13 is connected to an infusion tube with an indwell needle attached, and at the same time, the upstream branch tube 14 is connected to an infusion tube extended from a container containing the drug solution, similarly to the first embodiment described above. With the indwell needle inserted and remaining in the patient's body, the operation portions 45 are operated sending the drug solution from its container towards the patient to carry out administration of the drug solution to the patient. In this case, the two operation portions 45 are operated with a hand holding them from two sides. In addition, if another drug solution is to be provided to the patient in addition to the above drug solution fed from the container, the other drug solution is injected inside the chamber 31 from the confluent branching portion 12 through an infusion tube connected to the connector.

Figure 14:
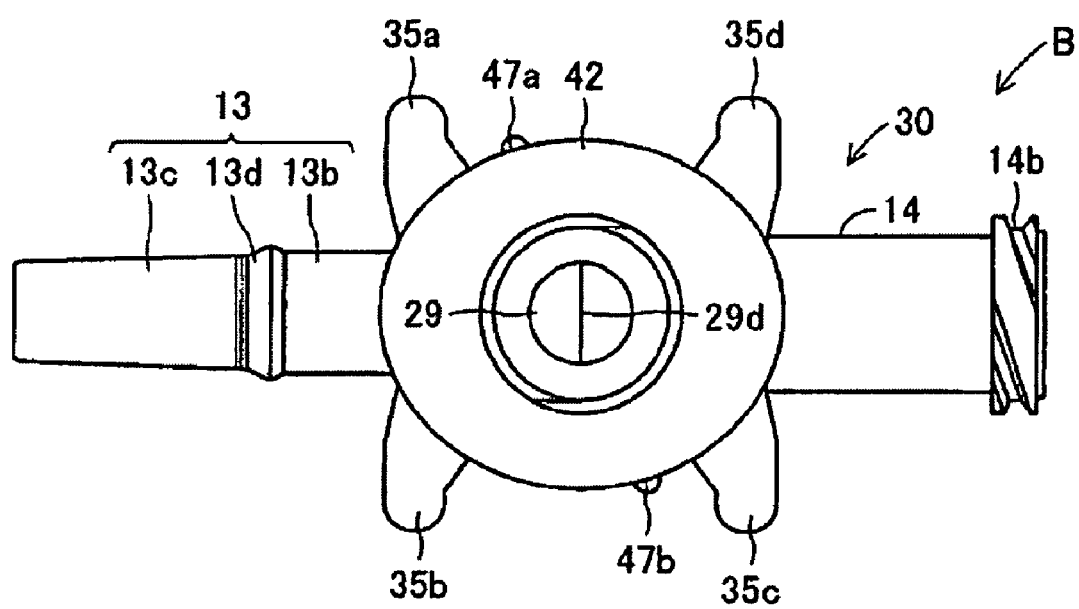
FIG. 14 is a plan view showing the liquid-mixing infusor in a state of the operation portion rotated in the counterclockwise direction.
Figure 15:
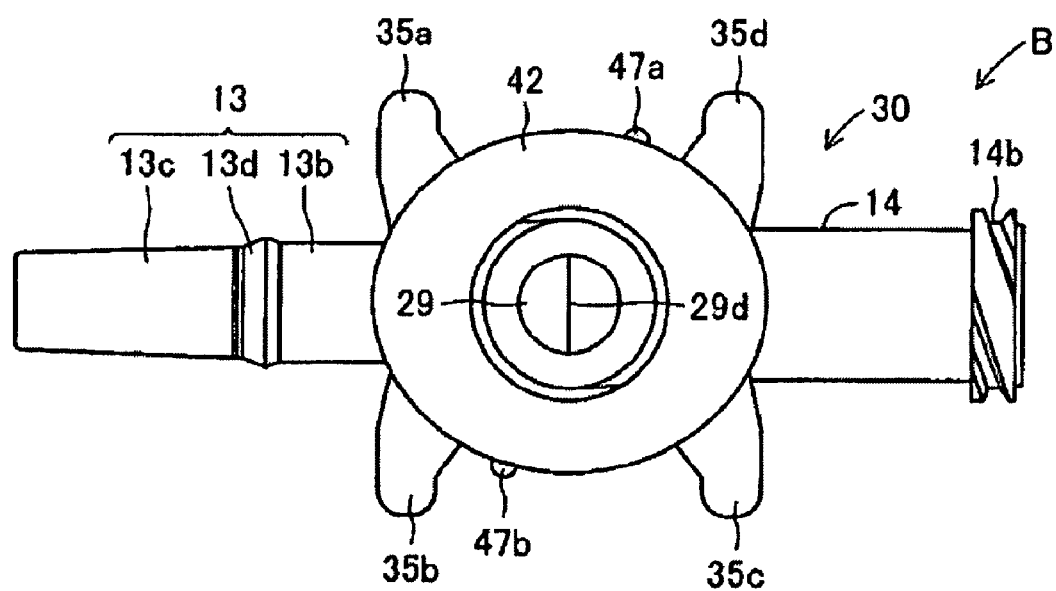
FIG. 15 is a plan view showing the liquid-mixing infusor in a state of the operation portion rotated in the clockwise direction.

In this case, the operation portions 45 are operated with the confluent branching portion 12 having a connector remaining attached to achieve the state shown in FIG. 14 or FIG. 15. As a result, the connector and the downstream branch tube 13 are connected through the connecting recess 22 inside the chamber 31. Incidentally, if the state of FIG. 14 is obtained by operating the operation portions 45, the lateral cross section of the liquid-mixing infusor B becomes same as that of FIG. 6, and if the state of FIG. 15 is obtained by operating the operation portions 45, the lateral cross section of the liquid-mixing infusor B becomes the same as that of FIG. 7. Furthermore, if the operation portions 45 are operated to obtain the state of FIG. 10 and FIG. 11, the connector, downstream branch tube 13 and upstream branch tube 14 are connected through the chamber 31.

In the liquid-mixing infusor B, the confluent branching portion 12 positioned at the top portion is fixed to the chamber 31 as explained above, the flow path formed inside the confluent branching portion 12 can be stabilized. Furthermore, the bottom ends of the handling extrusions 35a, 35b, 35c and 35d and a portion of the bottom portion of the chamber 31 are extended downwards from the bottom end of the main body portion of the chamber 31, it is possible to attach the liquid-mixing infusor B to an installation plate with the handling extrusions 35a, being fixed on the installation plate. Consequently, the operation portions 45 do not interfere with the installation of the liquid-mixing infusor B on an installation plate, and when the liquid-mixing infusor B is installed on an installation plate, the operation of the operation portions 45 becomes easy. Other reactions and effects of this liquid-mixing infusor B are same as those of the liquid-mixing infusor A described above.

Figure 16:
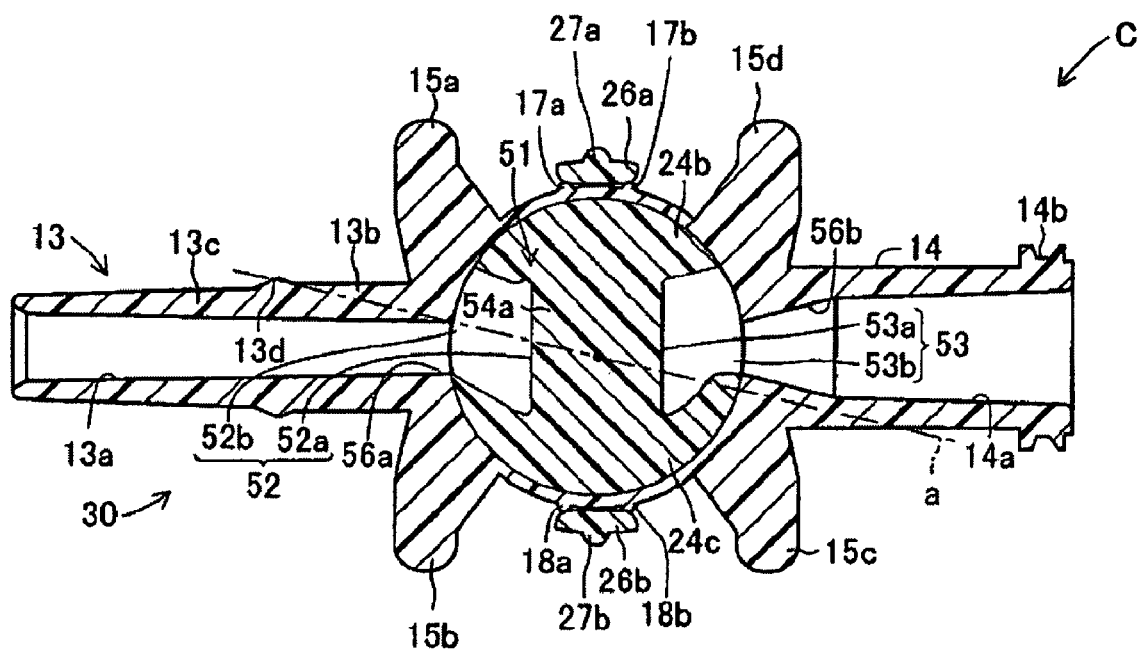
FIG. 16 is a cross section of a liquid-mixing infusor of the third embodiment.
Figure 17:
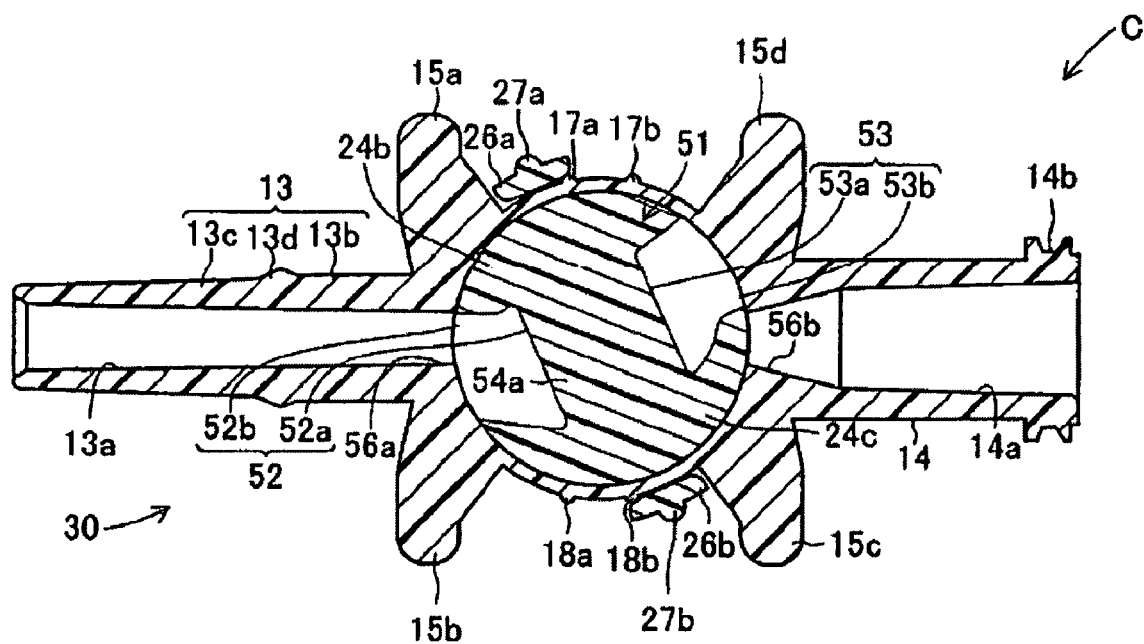
FIG. 17 is a cross section showing the liquid-mixing infusor in a state of the valve rotated in the counterclockwise direction from the state of FIG. 16.
Figure 18:
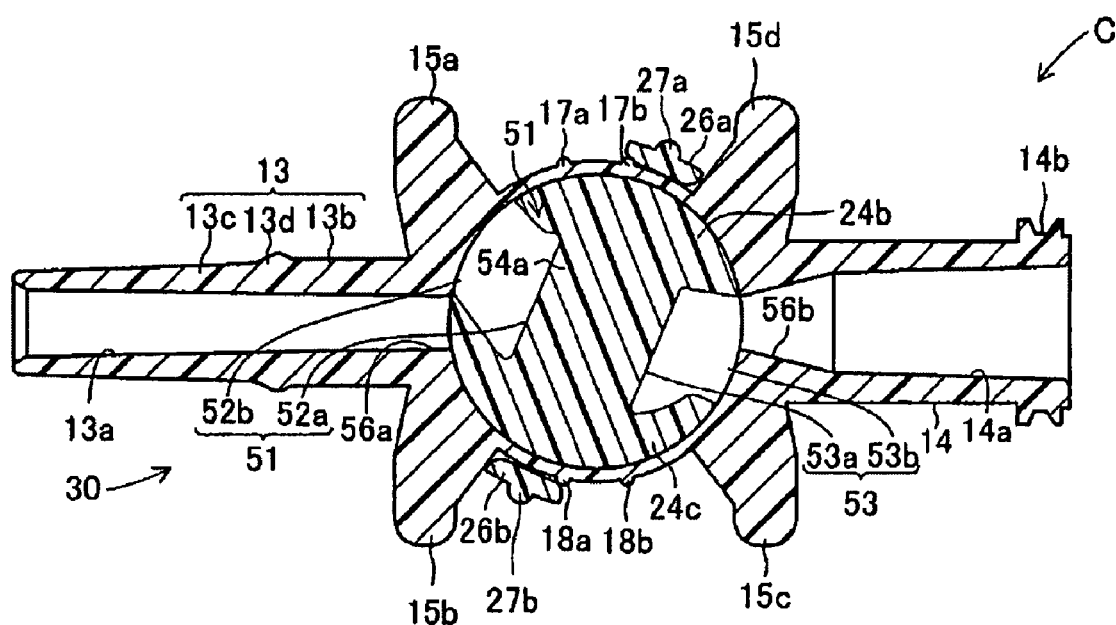
FIG. 18 is a cross section showing the liquid-mixing infusor in a state of the valve rotated in the clockwise direction from the state of FIG. 16.

FIGS. 16-18 show a liquid-mixing infusor C as the third embodiment of this disclosure. This liquid-mixing infusor C has a vertical cross section along the length direction the same as that shown in FIG. 13. In this liquid-mixing infusor C, a valve 51 is formed in a roughly cylindrical shape with recessed connecting sections 52 and 53 formed on two sides with the center axis of the cylinder in between. The widths of the recessed connecting sections 52 and 53 along the circumferential direction of valve 51 are set about equal, and the positions of the recessed connecting sections 52 and 53 are slightly shifted from the two sides with the center axis of the valve 51 in between on the peripheral surface of the valve 51.

Namely, the recessed connecting section 52 includes, similarly to the recessed connecting section 22, an upper recess 52*a* on the top side and connection hole 52*b* penetrating through the bottom portion of the upper recess 52*a* and peripheral surface of the valve 51. The width of the connection hole 52*b* along the circumferential direction is set to about twice as long as the diameter of the connection hole 56*a*, and the vertical length of the connection hole 52*b* is set about the same as the diameter of the connection hole 56*a*. Furthermore, the recessed connecting section 53 includes, similarly to the recessed connecting section 23, an upper recess 53*a* on the top side and connection hole 53*b* penetrating through the bottom portion of the upper recess 53*a* and peripheral surface of the valve 51. The width of the connection hole 53*b* along the circumferential direction is set to about twice the diameter of the connection hole 56*b*, and the vertical length of the connection hole 53*b* is set about the same as the diameter of the connection hole 56*b*.

Furthermore, the lateral cross-section of the recessed connecting section 52 in plan view is formed in a roughly square shape extending from the side of the vertical wall 54*a* towards the peripheral side twisted in the clockwise direction, and the lateral cross-section of the recessed connecting section 53 in plan view is formed in a roughly square shape extending from the side of the vertical wall 54*a* towards the peripheral side twisted in the counterclockwise direction. In addition, as shown in FIG. 16, when the front side portion of the recessed connecting section 52 (bottom side portion in FIG. 16) is allowed to face the connection hole 56*a*, the front side portion of the recessed connecting section 53 faces the connection hole 56*b*. Therefore, if the center of the peripheral side portion of the recessed connecting section 52 along the circumferential direction is allowed to be positioned on a hypothetical line a perpendicular to the central axis of the valve 51, the position of the center of the peripheral side portion of the recessed connecting section 53 is remote from the hypothetical line a.

If the valve 51 is allowed to rotate in the counterclockwise direction from the state of FIG. 16 to the state of FIG. 17, the rear side portion of the recessed portion connection 52 continues to face the connection hole 56*a*, but the recessed connecting section 53 is blocked. Furthermore, if the valve 51 is allowed to rotate in the clockwise direction from the state of FIG. 16 to the state of FIG. 18, the rear side portion of the recessed connecting section 53 continues to face the connection hole 56*b*, but the recessed connecting section 52 is blocked. According to this configuration, it is possible to connect both paths between the recessed connecting section 52 and connection hole 56*a* and between recessed connecting section 53 and connection hole 56*b*, block both of them or alternatively connect only one of the paths between the recessed connecting section 52 and connection hole 56*a* or between recessed connecting section 53 and connection hole 56*b*.

When a specific drug solution is to be administered to the patient with this configuration, the processing is similar to that carried out for the second embodiment described above. If another drug solution is to be mixed with the one from the upstream branch tube 14 by attaching a connector connected to an infusion tube to the confluent branching portion 12, the other drug solution supplied from the connector side is sent once to the upstream branch tube 14 side, adjusted to a suitable concentration on the upstream branch tube 14 side and subsequently allowed to flow to the downstream branch tube 13 side. In this case, the valve 51 is allowed to rotate connecting the chamber 13 and upstream branch tube 14 through the recessed connecting section 53 as shown in FIG. 18, and the path between the recessed connecting section 52 and downstream branch tube 13 is blocked.

Subsequently, the drug solution is supplied from the connector side to the side of the upstream branch tube 14 through the top branching portion 12 and recessed connecting section 53, and the drug solution is mixed with the drug solution fed to the upstream branch tube 14 from a container connected to the upstream branch tube 14. The valve 51 is allowed to rotate subsequently to achieve the state of FIG. 16 connecting the chamber 31 and upstream branch tube 14 through the recessed connecting section 53, and at the same time, the chamber 31 and downstream branch tube 13 through the recessed connecting section 52.

In the state as described above, the drug solution in a container connected to the upstream branch tube 14 is fed to the upstream branch tube 14, those two kinds of drug solutions mixed in the upstream branch tube 14 or a nearby portion flow in a mixed state to the side of the downstream branch tube 13 and are administered to the patient. Furthermore, even in the case of this liquid-mixing infusor C used, it is also possible to feed only a drug solution from a container connected to the upstream branch tube 14 to the downstream branch tube 13 or from the connector side to the downstream branch tube 13.

According to this liquid-mixing infusor C explained above, a drug solution supplied from the connector side is sent once to upstream branch tube 14 side, mixed with another drug solution fed from a container connected to the upstream branch tube 14, and the mixture is subsequently administrable to the patient's body. The flow path after two kinds of drug solutions are mixed and administered to the patient is sufficiently long for a uniform mixture those two kinds of drug solutions. As a result, the two kinds of drug solutions are administered to the patient in a uniformly mixed state. Other actions and effects of this liquid-mixing infusor C are similar to those of the liquid-mixing infusor B described above.

The liquid-mixing infusor of this disclosure is not necessarily limited to those embodiments described above, and suitable modifications are also possible. For example, in each of the embodiments described above, the rubber stopper 29 is allowed to have the slit 29*d* formed, and a connector is installed in the confluent branching portion 12 by inserting the male luer into the slit 29*d*, but instead of using a connector, it is possible to insert a syringe male luer or injection needle into the rubber stopper 29. If the injection needle is used, it is not necessary to form the slit 29*d* in the rubber stopper 29.

It is also possible to install windows for the downstream branch tube 13 and upstream branch tube 14 on the peripheral surface of the chamber 11 and apply indicators showing the state of connection and blocking of the paths between the chamber 11 and downstream branch tube 13, chamber 11 and upstream branch tube 14, on the peripheral surface of the valve 21, thus making it possible to see the indicators through the windows for confirmation. Consequently, the position of the rotary portion can be confirmed reliably. As an indicator in this case, it is possible to use, for example, characters such as "O" for open and "C" for closed. In addition, it is also possible to change the shapes of other portions, materials, suitably to configure the liquid-mixing infusor of this disclosure.

It will be understood that various modifications and changes in form and detail may be made to the embodiments of the present disclosure without departing from the spirit and scope of the disclosure. Therefore, the above description should not be construed as limiting the disclosure but merely as exemplifications of preferred embodiments thereof. Those skilled in the art will envision other modifications within the scope and spirit of the present disclosure as defined by the claims appended hereto. Having thus described the disclosure with the details and particularity required by the patent laws, what is claimed and desired protected is set forth in the appended claims.

What is claimed:

1. A liquid mixing infusor, which comprises:
a main body defining an internal chamber and having an upstream port, a downstream port and a confluent port, each port being fluidly couplable with the internal chamber;
a valve mounted within the internal chamber of the main body and adapted for rotational movement between a complete blocking position, wherein fluid flow between the upstream port and the downstream port, the upstream port and the confluent port and the downstream port and the confluent port is blocked, a partial blocking position, wherein fluid flow between the confluent port and one of the upstream port and the downstream port and between the upstream port and the downstream port is blocked, and a flow position permitting fluid flow between the upstream port and the downstream port; and
a manually manipulative member mounted relative to the main body and operatively connected to the valve, the manipulative member movable to cause corresponding movement of the valve between the complete blocking position, the partial blocking position and the flow position.

2. The liquid mixing infusor according to claim 1 wherein the valve is adapted for movement between first and second partial blocking positions, the first partial blocking position blocking fluid flow between the confluent port and the upstream port, the second partial blocking position blocking fluid flow between the confluent port and the downstream port.

3. The liquid mixing infusor according to claim 1 wherein the confluent port includes a closure seal.

4. The liquid mixing infusor according to claim 1 wherein the upstream port and the downstream port are arranged in general diametrical opposed relation along a reference longitudinal axis.

5. The liquid mixing infusor according to claim 4 wherein the confluent port is arranged about a reference vertical axis, the vertical axis extending between the upstream port and the downstream port, the confluent port vertically displaced relative to the upstream port and the downstream port.

6. The liquid mixing infusor according to claim 5 wherein the valve includes a vertical wall generally extending along the reference vertical axis, the vertical wall dimensioned to define an air trap when fluid flows between the upstream port and the downstream port.

7. The liquid mixing infusor according to claim 1 including positionable bosses corresponding to the complete blocking position, the partial blocking position and the flow position of the valve.

8. A liquid-mixing infusor, which comprises:
a main body defining an internal chamber arranged about a vertical axis;
a branching portion disposed vertically above the main body and having a connectable or interruptible flow path to the internal chamber, and a pair of branch tubes extending outwards from opposed sides of the main body and respectively having flow paths fluidly couplable with the internal chamber;
a valve disposed within the internal chamber and rotatable about the vertical axis between a first position permitting fluid flow between the pair of branch tubes and the internal chamber, a second position blocking fluid flow between the pair of branch tubes and permitting fluid flow between a first of the pair of the branch tubes and the internal chamber, and a third position blocking fluid flow between the pair of branch tubes and the internal chamber; and
a rotary portion extending external of the internal chamber from the valve and having an operation portion, the operating portion being adapted for manual manipulation to cause corresponding rotatable movement of the valve between the first position, the second position, and the third position.

9. The liquid mixing infusor according to claim 8 wherein the operation portion includes a cap-shaped body attached rotatably to the main body.

10. The liquid mixing infusor according to claim 9 wherein the valve includes a pair of blocking sections blocking fluid flow between a second of the pair of the branch tubes and the internal chamber when the valve is in the second position thereof, and a pair of depressed connection sections connecting between the pair of branch tubes and the internal chamber when the internal valve is in the first position.

11. The liquid mixing infusor according to claim 10 wherein a first of the pair of the depressed connecting sections is in general alignment with a corresponding first of the pair of the branch tubes when in the second position of the valve to thereby fluidly couple the branching portion with the first of the pair of the branch tubes.

12. The liquid mixing infusor according to claim 11 wherein the valve is adapted to rotate about the vertical axis to a fourth position wherein a second of the pair of the depressed connecting sections is in general alignment with a corresponding second of the pair of the branch tubes to thereby fluidly couple the branching portion with the second of the pair of the branch tubes.

13. The liquid mixing infusor according to claim 12 wherein the main body defines a circumferential surface having positioning bosses, and the operation portion having stops engageable with the positioning bosses and wherein respective positioning bosses and stops correspond to the first, second, third and fourth positions of the valve.

14. The liquid mixing infusor according to claim 8 the branching portion includes a closure element adapted to permit an insertion tube to pass therethrough.

15. The liquid mixing infusor according to claim 10 wherein widths of the pair of depressed connecting sections along the rotational direction are set to be different permitting one of the pair of branch tubes to be connected to the internal chamber when the valve is in the second position.

16. A liquid-mixing infusor, which comprises:
a main body defining an internal chamber arranged about a vertical axis;
a branching portion disposed vertically above the main body and defining a flow path to the internal chamber, and a pair of branch tubes extending outwards from opposed sides of the main body and respectively having flow paths fluidly couplable with the internal chamber;
a valve disposed within the internal chamber and movable about the between a first position permitting fluid flow between the pair of branch tubes and the internal chamber, a second position preventing fluid flow between the pair of branch tubes while permitting fluid flow between a first of the pair of the branch tubes and the internal chamber, and a third position preventing fluid flow between the pair of branch tubes and the internal chamber; and a manually manipulative member mounted relative to the main body and operatively connected to the valve, the manipulative member movable to cause corresponding movement of the valve between the first position, the second position and the third position.

17. The liquid mixing infusor according to claim 16 wherein the valve is dimensioned and adapted to rotate about the vertical axis to move between the first position, the second position and the third position.

* * * * *